United States Patent
Miller

(10) Patent No.: US 6,662,049 B1
(45) Date of Patent: Dec. 9, 2003

(54) IMPLANTABLE DEVICE WITH A PROGRAMMABLE RESET MODE AND METHOD OF OPERATION

(75) Inventor: Leslie S. Miller, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 08/992,738

(22) Filed: Dec. 17, 1997

(51) Int. Cl.[7] ............................................... A61N 1/37
(52) U.S. Cl. .......................................... 607/27; 607/30
(58) Field of Search ............................. 607/27, 28, 29, 607/63, 30, 31, 32

(56) References Cited

U.S. PATENT DOCUMENTS

| | | | |
|---|---|---|---|
| 4,208,008 A | 6/1980 | Smith | 371/15 |
| 4,390,022 A | * 6/1983 | Calfee et al. | 607/16 |
| 4,463,760 A | 8/1984 | Elmovist | 128/419 |
| 4,567,892 A | 2/1986 | Plicchi et al. | 128/419 |
| 4,613,937 A | 9/1986 | Batty, Jr. | 364/413 |
| 4,958,632 A | 9/1990 | Duggan | 128/419 |
| 4,966,146 A | 10/1990 | Webb et al. | 128/419 |
| 5,226,413 A | 7/1993 | Bennett et al. | 128/419 |
| 5,456,691 A | 10/1995 | Snell | 607/30 |
| 5,456,692 A | 10/1995 | Smith, Jr. et al. | 607/31 |
| 5,607,458 A | * 3/1997 | Causey, III et al. | 607/27 |

FOREIGN PATENT DOCUMENTS

JP    5-56936 A    3/1993

* cited by examiner

*Primary Examiner*—William E. Kamm
*Assistant Examiner*—Kennedy J. Schaetzle

(57) ABSTRACT

An implantable cardiac stimulation system operates in one of at least two modes, a normal mode and a reset mode, wherein the control parameters for the reset mode are programmable. In the event of an error in operation, the implantable system switches from the normal mode to the reset mode. The programmability of the parameter values of the reset mode allows a physician to customize the operation of the pacemaker in the reset mode to meet the particular therapeutic needs of a patient in the event of an error in operation. In a preferred embodiment, the parameter values for the normal mode of operation are stored in a volatile memory unit, whereas the parameter values for the reset mode of operation are stored in a non-volatile memory unit.

4 Claims, 2 Drawing Sheets

IMPLANTABLE DEVICE WITH A PROGRAMMABLE RESET MODE AND METHOD OF OPERATION

FIELD OF THE INVENTION

The present invention relates generally to implantable devices such as a cardiac pacemaker. More particularly, this invention relates to a programmable implantable device having a plurality of operating modes.

BACKGROUND OF THE INVENTION

Improper heart function can often be remedied by the use of an implantable device such as a pacemaker. These devices generally provide an electrical pulse to a selected area of the heart that is not (in terms of timing or strength) adequately receiving its natural pulse. Under abnormal cardiac conditions, and particularly cardiac rhythm disturbances, pacemaker therapy is applied to remedy several forms of cardiac arrhythmias (rhythm disturbances) including bradycardias, AV conduction block, supraventricular tachycardias, and atrial and ventricular ectopic arrhythmias. There are essentially two types of pacemakers: single-chamber (capable of sensing and pacing in either the atrium or the ventricle only); and dual-chamber (capable of sensing and pacing in both the atrium and the ventricle). From a practical standpoint, there are essentially only two forms of single-chamber pacing: VVI (senses and paces in the ventricle) and AAI (senses and paces in the atrium). On the other hand, there are many modes of dual-chamber pacing such as VDD (paces in the ventricle only, senses in the atrium and ventricle), DVI (paces in the atrium and ventricle, and senses in the ventricle only), DDI (senses and paces in both the atrium and ventricle), and DDD (senses and paces in both the atrium and ventricle, with an inhibited and triggered response to sensing). A letter "R" is sometimes added to these pacemaker modes to indicate the pacemaker's ability to provide rate-modulated (also sometimes called rate-responsive or rate-adaptive) pacing. For instance, a DDDR pacemaker is capable of adapting to the need to increase a patient's heart rate in response to physiologic stress, even if the patient's intrinsic SA node would not normally allow this to occur.

Modern pacemakers typically incorporate a microprocessor and one or more memory units. These pacemakers are configured to allow remote programming after implantation in the patient's body, and offer advanced features such as sensor-control, programmable dual-chamber pacing and sensing, and rate-modulated cardiac pacing. External and noninvasive programming is accomplished using telemetry circuits which allow a clinician to communicate with and program the implanted pacemaker using an external programmer. Examples of programmable pacemaker functions include the pacing mode, rate, and pulse voltage and width. To program a pacemaker externally, signals (usually pulsed magnetic fields or radio frequency signals) are transmitted through the patient's skin between the programmer and the pacemaker's control unit.

Microprocessor-based pacemakers have proven to be of great practical utility, because they do not impose unneeded trauma on the heart and they provide therapy on as-needed basis. However, these devices do occasionally suffer from malfunction and error. Such malfunction or error is often of significant concern, because a person's life may depend on the device's proper operation. In these devices, errors could be caused by a malfunction in the hardware (the electronics) or by deterioration in the software, which might occur over time due to a memory or power failure.

To reduce the severity of such malfunctions, some pacemakers have been designed to automatically transition to a "fail-safe", pacing mode upon the detection of certain errors. In this mode, commonly referred to as a "reset mode," the programmable, "normal mode" parameters are effectively replaced with a fixed set of default or "reset mode" parameters. ("Parameters" are stored values that specify the pacing therapy that is to be administered by the pacemaker.) The reset mode parameters typically include, for example, the pacing rate, the pulse width, and the pulse amplitude to be used in the reset mode. The general goal of operating in a reset mode is to eliminate the pacemaker's dependence on the malfunctioning component (such as a corrupted or defective memory area), while continuing to apply a pacing therapy to the heart.

Although the above-described approach allows the patient to continue to receive therapy, the pacing therapy applied in the reset mode is not always adequate, particularly in patients that suffer from tachyrhythmia, bradycardia, and atrial fibrillation. In addition, the pre-set voltage provided to the heart in the reset mode can be too high for the particular patient, and may therefore interfere with the heart's normal operation and/or unnecessarily reduce the life of the battery.

SUMMARY OF THE INVENTION

One partial solution to the above-described problem has been to provide a reset mode which preserves some of the automaticity functions of the pacemaker. ("Automaticity" refers generally to the ability of a pacemaker to make logical decisions and adjust pacing therapies based on physiological variations within the patient.) One problem with this approach is that the parameters that govern reset mode operation are typically stored in a read-only memory (ROM), and thus cannot be programmed by the clinician. Thus, although the pacemaker automatically adjusts the reset mode therapy according to the patient's symptoms, these adjustments are made according to a pre-specified pacing program, and the clinician cannot customize this program to individual patients.

The present invention overcomes the aforementioned and other problems by providing an implantable system and associated method that allow programming of the reset parameters, thereby allowing a physician to customize the reset mode in conformance with the particular therapeutic needs of a patient. The present invention thereby provides a safer, more reliable implantable system.

In accordance with one form of the invention, an implantable system includes a pulse generator, mode switching means, and external programming means. The pulse generator senses the electrical activity in the heart, recognizes certain needs for the electrical stimulation, and delivers the appropriate pulses with sufficient energy to initiate depolarization of the cardiac tissue. The mode switching means monitors the operation of the implantable system and, upon detecting a malfunction, switches the system from the normal mode to the reset mode of operation. The programming means allow a clinician to program the parameters for the normal and reset modes of operation.

To perform its functions, the pulse generator includes a microprocessor-based controller for determining the proper timing of electrical stimuli that are provided to the heart. The pulse generator further includes two or more memories where it stores program parameters for controlling the normal mode and reset mode of operation. A first programmable memory is utilized to store a set of "normal mode" parameters that specify a full-featured mode of operation, and a second programmable memory which stores a set of "reset mode" parameters. Both sets of parameters are initially set at the factory, and can thereafter be modified by telemetry (before and/or after implantation) by the clinician. The programmable parameters include the pacing mode, pacing rate, sensor status, pulse configuration, sensitivity level, and several others. Because the reset parameters are programmable, a fail-safe or reset mode is provided that can be customized to meet the specific therapeutic needs of a particular patient.

In response to detected errors, the switching means switch the mode of operation of the implantable system from the normal mode to the reset mode. In doing so, the normal operating mode parameters are ignored and the pulse generator becomes governed by the reset operating parameters. This switchover minimizes the probability of, or in certain circumstances completely eliminates, the use of defective components in the pacemaker. By providing the clinician with the ability to program the reset operating parameters, the present invention allows the particular therapeutic needs of the patient to be served in the event of a malfunction in the implanted pacemaker.

BRIEF DESCRIPTION OF THE DRAWINGS

The above and other aspects, features and advantages of the present invention will be better understood by referring to the following detailed description of a particular preferred embodiment, which should be read in conjunction with the accompanying drawings. The detailed description is not intended to limit the enumerated claims, but to serve as a particular example thereof.

DETAILED DESCRIPTION OF THE PREFERRED EMBODIMENT

Reference is now made to the drawings wherein like numerals refer to like parts throughout this application.

Figure 1:
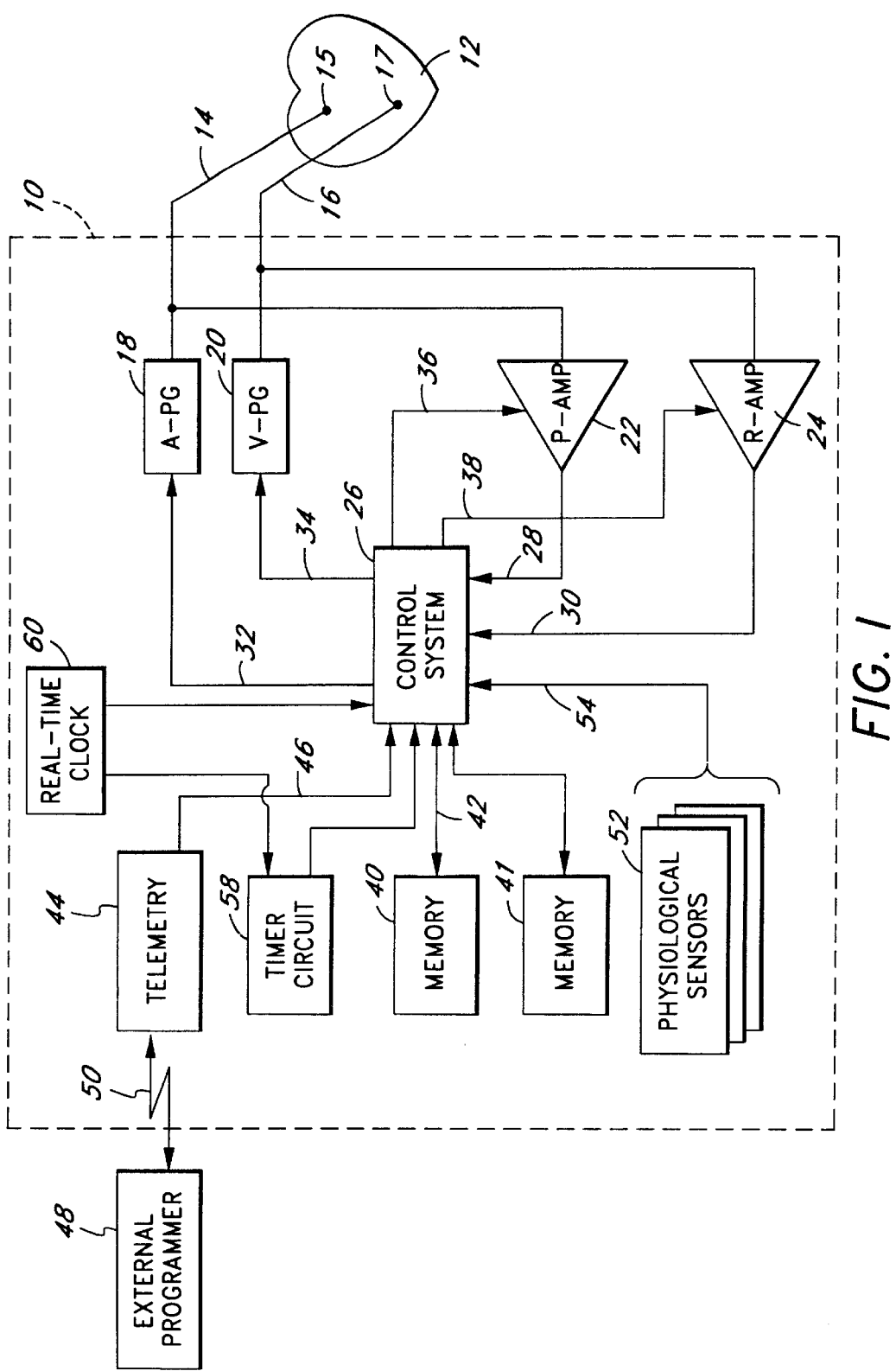
FIG. 1 shows a functional block diagram of an exemplary cardiac stimulation device made in accordance with the present invention.

FIG. 1 is a functional block diagram of an exemplary implantable cardiac stimulation device in accordance with the present invention. The device illustrated in FIG. 1 is a dual-chamber rate-responsive pacemaker. The pacemaker 10 is referred to as a dual-chamber pacemaker because it interfaces with both the atria and the ventricles of the heart 12. This pacemaker 10 is only illustrative of one type of pacemaker with which the present invention may be used. Other kinds of implantable stimulation devices may be used with the present invention including, without limitation, DDD, DVI, VDD, VAI, AAI, and VVI pacemakers, whether rate-responsive or not. As shown in FIG. 1, the implantable stimulation device comprises a control system 26, two or more memory units 40 and 41, a telemetry unit 44, an atrial pulse generator ("A-PG") 18, a ventricular pulse generator ("V-PG") 20, an atrial channel sense amplifier ("P-AMP") 22, a ventricular channel sense amplifier ("R-AMP") 24, a lead network comprising leads 14 and 16, a tissue-heart interface comprising two or more electrodes 15 and 17, one or more physiological sensors 52, a timer circuit 58, a real-time clock 60, and an external programmer 48.

The pacemaker 10 is connected to a heart 12 by the lead network. Lead 14 has an electrode 15 at its end which is in contact with one of the atria of the heart 12. Lead 16 has another electrode 17 at its end which is in contact with one of the ventricles of the heart 12. The leads 14 and 16 carry stimulating pulses to the electrodes 15 and 17 from A-PG 18 and V-PG 20 respectively. In addition, the leads 14 and 16 carry intrinsic electrical signals from the atrium and ventricle to the P-AMP-22 and the R-AMP 24, respectively. Hence, the pacemaker 10 uses the lead network to transmit and receive electrical signals to and from the heart 12.

The operation of the dual-chamber rate-responsive pacemaker 10 is controlled by a control system 26, which is preferably an 8-bit microprocessor. The control system 26 receives output signals from the atrial and ventricular amplifiers P-AMP 22 and R-AMP 24 via signal lines 28 and 30, respectively. Typically, the respective pulse signals are generated on signal lines 28 and 30 each time a P-wave or an R-wave is sensed within the heart 12. Based on the timing of these sensed signals, the control system 26 generates trigger signals which are sent to A-PG 18 and V-PG over signal lines 32 and 34, respectively. These trigger signals are generated each time it is determined that pulse signals are to be generated by the atrial and ventricular pulse generators A-PG 18 and V-PG 20 to stimulate the heart 12. The atrial trigger signal is referred to simply as the "A-pulse," and the ventricular trigger signal is referred to as the "V-pulse." During the time that either an A-pulse or V-pulse is being delivered to the heart 12, the corresponding amplifier, P-AMP 22 or R-AMP 24, is disabled. It is the control system 26 which disables these amplifiers using blanking signals delivered to P-AMP 22 and/or R-AMP 24 over signal lines 36 and 38, respectively. The purpose of this blanking action is to prevent the amplifiers P-AMP 22 and R-AMP 24 from becoming saturated from the relatively large stimulation pulses that are present at their input terminals during pulse generation. In addition, this blanking action helps prevent residual electrical signals present in the muscle tissue as a result of the pacemaker's own stimulation from being interpreted by the control system 26 as P-waves or R-waves.

The pacemaker 10 further includes one or more physiologic sensors 52 connected to the control system 26 by a suitable connection line 54. While these sensors 52 are illustrated as being within the pacemaker 10, one or more of these sensors can be external to the pacemaker 10. A common type of sensor is an activity sensor, such as a piezoelectric crystal, mounted externally to the casing of the pacemaker. Other types of physiologic sensors which may be included are those which sense oxygen content of the blood, respiration rate, pH of the blood, body motion, myocardial depolarization time interval, and the like. Any one, or a combination, of these sensors may be used with the present invention. Rate-responsive (also known as rate-modulated or rate-adaptive) pacing helps a patient adapt to physiologic stress with an increase in heart rate, even if the patient's intrinsic sinus node would not normally allow this to occur. One or more sensors 52 are used to adjust the rate (escape interval) of the pacemaker 10 in a manner that tracks the activity of the patient.

Furthermore, as shown in FIG. 1, the telemetry unit 44 is connected to the control system 26 by way of a suitable command/data bus 46. In turn, the telemetry unit 44, which is typically built-in within the implantable device, may selectively communicate with an external programmer 48 such as the APS III Programmer available from Pacesetter, Inc., using an appropriate wireless communication link 50. Using the programmer 48, data may be remotely received from and transmitted to the pacemaker 10. Typically, such data is either held within the control system 26, as in a data latch, or stored within one or more memory units 40 and 41. In this manner, communication can be established noninvasively with the implanted pacemaker 10 from a remote, non-implanted location. The form of communication used by the external device 48 to instruct the pacemaker 10 is often referred to as "interrogation."

Using the external programmer 48, desired control commands may be transmitted to the control system 26 over the control link 50 to program the pacemaker. Using the external programmer 48, a trained clinician programs values of the parameters for both the normal and reset modes of operation to more particularly meet the therapeutic needs of the patient. The parameters for the normal and reset modes govern the operation of the pacemaker 10 in both modes of operation, respectively. The programmer 48 incorporates a set of software instructions that allow a clinician to interactively view and modify the normal mode and reset mode parameters. Upon interrogation, and preferably immediately, the pacemaker 10 indicates the mode of operation it is operating in to the programmer 48.

The values of the normal mode and reset mode parameters can be set by the physician within acceptable ranges which are preset at the factory. In the preferred embodiment, the ranges of the parameter values for the reset mode are narrower than the ranges of the parameter values for the normal mode of operation. Using a narrower range of parameter values for the reset mode prevents the clinician from accidentally applying a parameter value which might activate an already defective component in the implantable device. Hence, the probability of using a defective component upon detection of a malfunction in the implantable device is minimized. A list of the typical parameters for the normal and reset modes, and their exemplary values for both modes may also be programmed by the clinician prior to implantation or after implantation. Table 1 shows a list of the programmable operation parameters in the normal and reset modes with their exemplary values/ranges.

| Parameters | Normal Mode | Reset Mode |
| --- | --- | --- |
| Mode | DDD | VVI |
| Sensor | OFF | PASSIVE[1] |
| Rate (ppm) | 60 | 70 |
| AV Delay (ms) | 175 | N/A -> 175 |
| Max Track Rate (ppm) | 110 | N/A -> 110 |
| V Pulse Configuration[2] | Bipolar | Unipolar |
| V Pulse Width (ms) | 0.4 | 0.6 |
| V Pulse Amplitude (V) | 4 | 4.5 V |
| V Sense Configuration[2] | Bipolar | Unipolar |
| V Sensitivity (mV) | 2 | 2 |
| V Retractory (ms) | 250 | 325 |
| A Pulse Configuration[2] | Bipolar | N/A -> Unipolar |
| A Pulse Width (ms) | 0.4 | N/A ->0.6 |
| A Pulse Amplitude (V) | 4 | N/A -> 4 |
| A Sense Configuration[2] | Bipolar | N/A -> Unipolar[3] |
| A Sensitivity (mV) | 1 | N/A -> 1 |
| A Retractory (ms) | 275 | N/A -> 275 |
| Blanking (ms) | 38 | N/A -> 38 |
| V Safety Option | ENABLE | N/A -> ENABLE |
| PVC Options | "+PVARP" | N/A -> "+PVARP" |
| PMT Options | OFF | N/A -> OFF |
| RRAVD | DISABLE | N/A -> DISABLE |
| Magnet[4] | ON | TEMP OFF |
| Threshold[5] | 2 | N/C |
| Slope[5] | 8 | N/C |
| Max Sensor Rate[5] (ppm) | 110 | N/C |
| Reaction Time[5] | Fast | N/C |
| Recovery Time[5] | Medium | N/C |

-continued

| Parameters | Normal Mode | Reset Mode |
| --- | --- | --- |

[1]If the sensor has been programmed to ON, it will be autoprogrammed to PASSIVE.
[2]Information stated applies to model 2028 only. Model 2029 has only unipolar pulse and sense configuration in both chambers.
[3]Unipolar tip.
[4]If magnet ON has been selected, the pulse generator will revert to magnet TEMPORARY OFF after interrogation or programming. Refer to the Magnet Operation section of this manual for more information.
[5]These values are autoprogrammed by sensor parameter RTS.
N/A = Parameter not applicable in this mode; N/C = No change.

Furthermore, as shown in FIG. 1, the control system 26 accesses the two memory units 40 and 41 via data/address bus lines 42 and 43, respectively. The set of parameters for the normal mode is preferably stored in the first memory unit 40, which is a programmable memory. The normal mode parameters may be programmed at the factory and/or by telemetry (before and/or after implantation). The first memory unit 40 is preferably a volatile memory such as a random access memory ("RAM")

The set of parameters for the reset mode is preferably stored in the second memory unit 41, which is also a programmable/writable memory. The reset mode parameters may be programmed at the factory and/or by telemetry (before and/or after implantation). An important feature of the present invention is the ability of the clinician to program the set of parameters for the reset mode to meet the specific therapeutic needs for a particular patient. The set of parameters is stored as a default set which the pacemaker 10 resorts to in case of error in operation. To enable programmability, it is preferable to have the second memory unit 41 be a non-volatile memory such as a programmable read only memory (PROM), an erasable programmable read only memory (EPROM), a flash-electric static random access memory (FRAM), a flash erasable programmable read only memory (FEPROM), or other similar memories incorporating non-volatile memory technology.

In the normal mode of operation, the pacemaker 10 is able to provide a full-featured therapy program that incorporates substantially all of the pacemaker's programmable and "automaticity" type functions. In particular, the pacing therapy is programmed by a clinician to be especially suited to the needs of the patient under treatment, and may also be adjusted in accordance with data gathered from the patient's heart by the pacemaker 10. The exemplary events which trigger or cause the pacemaker 10 to switch from the normal mode to the reset mode of operation include sensor failure, power or voltage drop (e.g. due to low ambient temperature), error in or corruption to the parameter values for the normal mode, RAM failure, and other component-level or module-level failures.

When the reset mode is triggered, the operation of the pacemaker 10 is governed by the reset mode parameters which have been programmed by the clinician to meet the therapeutic needs of the patient. Hence, after switching to the reset mode, the pacemaker 10 may, for example, apply a particular pacing mode (e.g., DDD, programmed by the clinician for the reset mode) instead of a more sophisticated pacing mode (e.g., DDDR which is programmed for the normal mode). The pacemaker 10 thereby avoids the use of the damaged physiological sensors 52 (which were required in the DDDR pacing mode), while maintaining a pacing therapy in the reset mode which still meets the particular needs of the patient.

The switchover is triggered by the detection of a predefined type of error, such as an address error, a parity error, an opcode error, or a time-out error. Methods for detecting these and other types of errors are well known in the art. In this exemplary configuration, a timer circuit 58 is incorporated to determine when a time-out occurs while the device is in the normal mode of operation. The time-out is typically set to an interval of two seconds. If a time-out occurs, the timer circuit 58 triggers the control system 26 to ignore the normal mode parameters, and apply the reset mode parameters. Thus, the control system 26 ignores data which was stored (prior to switching over) in the memory unit 40. In the reset mode, the control system 26 retrieves data from the memory unit 41, and may still use the memory unit 41 as a scratch pad to perform a calculation, or to store data collected from the patient's heart. Alternatively, a system interrupt may be telemetrically issued by the clinician to switch the pacemaker 10 from the normal mode to the reset mode of operation, or vice versa.

Figure 2:
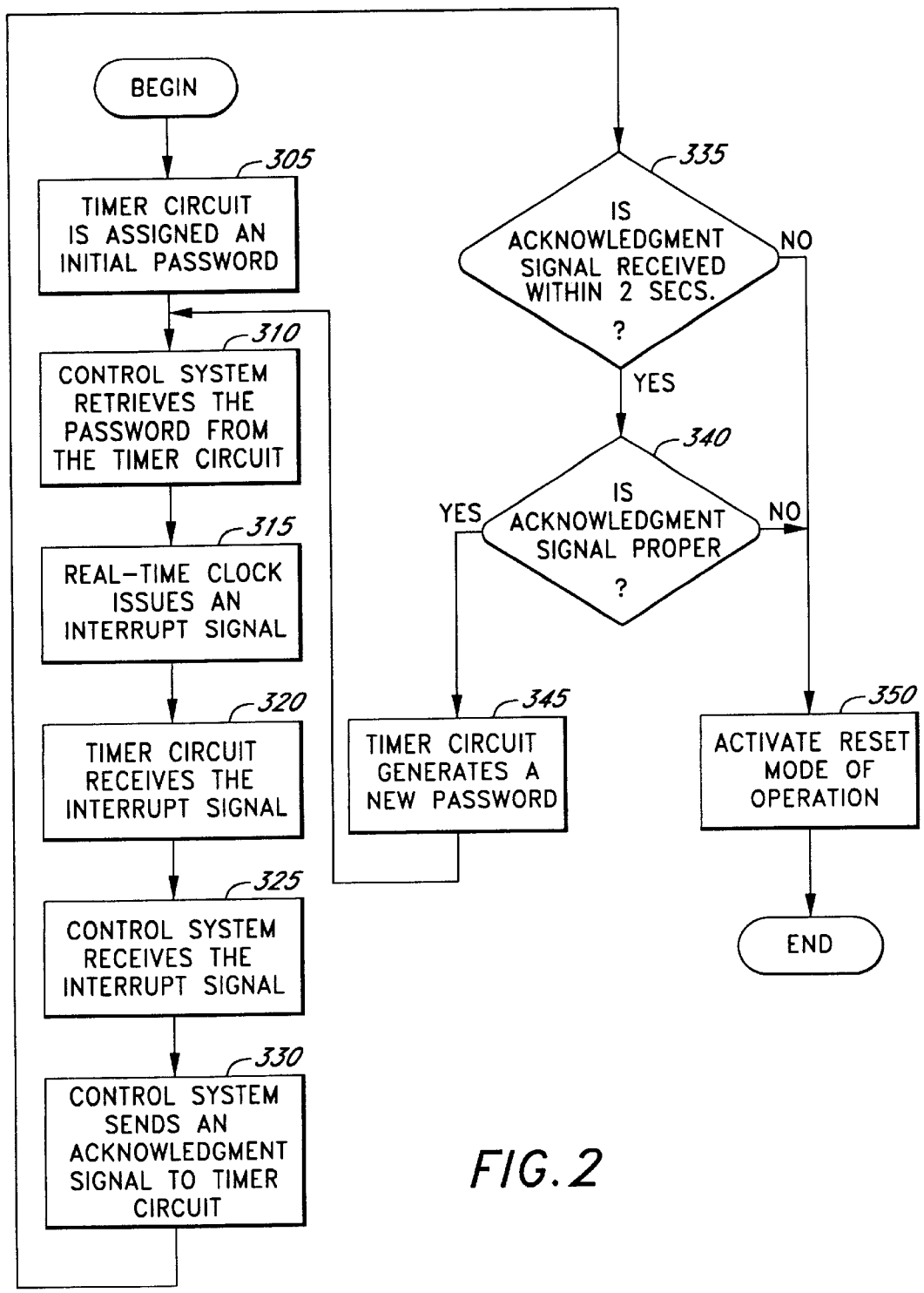
FIG. 2 is a flow chart illustrating the steps of switching between the various modes of operation of the preferred embodiment.

Now referring to FIG. 2, exemplary steps of the operation of the switching process are introduced. As discussed above, the control system 26 is typically provided with two alternative sets of operating parameters. The first set of parameters is for the normal mode, and the second set of parameters is for the reset mode of operation. FIG. 2 illustrates the steps of one of a variety of methods used by the pacemaker to determine which set of parameters to apply. At step 305, the timer circuit 58 is assigned an initial password for use by the control system 26 in its acknowledgment signals. It is preferable that the password comprises 8 bits having a randomly generated 6-bit key and a 2-bit address code. The 2-bit address code specifies one of four possible addresses within the timer circuit 58, and the 6-bit key is a randomly generated code. Typically, after a system reset, the initial password is an 8-bit password in which all bits are "zeros." At step 310, the control system 26 retrieves this password for use in the next acknowledgement. At step 315, a real time clock 60 (FIG. 1) issues an interrupt signal preferably every two seconds. The control system 26 responds to the interrupt signal which is issued every two seconds by the real time clock 60 (FIG. 1). At steps 320 and 325, the interrupt signal is received by the timer circuit 58 and the control system 26, respectively.

At step 330, the control system 26 sends an acknowledgement signal to the timer circuit 58 before the next interrupt signal is issued by the real time clock 60. The acknowledgement signal comprises the 8-bit password having the 6-bit key and the 2-bit address code. In order to properly acknowledge the interrupt, the control system 26 provides the 6-bit key to the address designated by the 2-bit address code. At step 335, the timer circuit 58 first determines if the acknowledgement signal is received from the control system 26 within two seconds of the issuance of the interrupt signal. If the acknowledgment is not received within two seconds, the pacemaker 10 is set to the reset mode of operation at step 350. If the acknowledgement signal is received within two seconds, the timer circuit determines if its a proper acknowledgement at step 340. If the acknowledgement is not proper, the pacemaker 10 is set to the reset mode of operation at step 350. If the acknowledgement signal is proper, the timer circuit 58 generates a new password comprising a new key and a new address code at step 345. The process begins again with the retrieval of the new password by the control system 26 from the timer circuit 58.

In view of the foregoing, it will be appreciated that the present invention overcomes the longstanding need for maintaining a customized therapy despite the activation of a reset mode of an implantable device in response to detected errors in operation. The present invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An implantable cardiac stimulation device, comprising:

a pulse generator which generates a stimulation therapy for application to the heart of a patient, the device being switchable between at least two modes of operation including a normal mode and a reset mode, with each mode being controlled at least in part by a respective set of program parameters, and the reset mode corresponding to a fail-safe therapy program which enables the patient to continue receiving a customized stimulation therapy when a malfunction in the normal mode occurs;

mode switching means which monitors the operation of the device in the normal mode and, upon detecting the malfunction, switches the device from the normal mode to the reset mode; and programming means for enabling a clinician to program at least a portion of the set of program parameters corresponding to the reset mode.

2. The device as defined in claim 1, wherein the set of program parameters corresponding to the reset mode is programmable in non-volatile storage means, and the set of parameters corresponding to the normal mode is programmable in volatile storage means.

3. A method of maintaining an effective therapy of an implantable pacemaker when a malfunction occurs therein, the method comprising the steps of:

providing a pacemaker comprising a pulse generator, and comprising first and second memories for storing first and second sets of program parameters, respectively, the first set of parameters being applied to control a therapy program during a normal operation of the pacemaker, and the second set of parameters being applied to control the therapy program during a reset operation of the pacemaker;

monitoring the operation of the pacemaker to determine if a malfunction has occurred in the normal operation thereof, and switching the pacemaker to the reset operation upon detecting the malfunction; and providing clinician programming of at least the second set of program parameters.

4. The method as defined in claim 3, wherein the second set of program parameters is programmable in non-volatile storage, and the first set of parameters is programmable in volatile storage.

* * * * *